(12) United States Patent
Jo et al.

(10) Patent No.: US 11,246,561 B2
(45) Date of Patent: Feb. 15, 2022

(54) PULMONARY EDEMA MONITORING APPARATUS

(71) Applicant: SEOUL NATIONAL UNIVERSITY HOSPITAL, Seoul (KR)

(72) Inventors: You Hwan Jo, Seongnam-si (KR); Jae Hyuk Lee, Seongnam-si (KR); Hyuk Sool Kwon, Seongnam-si (KR)

(73) Assignee: SEOUL NATIONAL UNIVERSITY HOSPITAL, Seoul (KR)

( * ) Notice: Subject to any disclaimer, the term of this patent is extended or adjusted under 35 U.S.C. 154(b) by 0 days.

(21) Appl. No.: 16/640,951

(22) PCT Filed: Dec. 21, 2018

(86) PCT No.: PCT/KR2018/016404
§ 371 (c)(1),
(2) Date: Feb. 21, 2020

(87) PCT Pub. No.: WO2019/132434
PCT Pub. Date: Jul. 4, 2019

(65) Prior Publication Data
US 2020/0170613 A1 Jun. 4, 2020

(30) Foreign Application Priority Data
Dec. 26, 2017 (KR) .................. 10-2017-0179547

(51) Int. Cl.
*A61B 8/08* (2006.01)
*A61B 8/00* (2006.01)

(52) U.S. Cl.
CPC .............. *A61B 8/08* (2013.01); *A61B 8/4236* (2013.01); *A61B 8/4281* (2013.01);
(Continued)

(58) Field of Classification Search
None
See application file for complete search history.

(56) References Cited

U.S. PATENT DOCUMENTS

| | | | |
|---|---|---|---|
| 2008/0275349 A1* | 11/2008 | Halperin | A61B 5/447 600/484 |
| 2011/0009746 A1* | 1/2011 | Tran | A61B 8/08 600/437 |

(Continued)

FOREIGN PATENT DOCUMENTS

| | | |
|---|---|---|
| JP | 2010-534548 A | 11/2010 |
| JP | 2010-537767 A | 12/2010 |

(Continued)

OTHER PUBLICATIONS

International Search Report dated Apr. 8, 2019, corresponding to International Application No. PCT/KR2018/016404.

(Continued)

*Primary Examiner* — Oommen Jacob
*Assistant Examiner* — Shahdeep Mohammed
(74) *Attorney, Agent, or Firm* — Hauptman Ham, LLP

(57) ABSTRACT

Provided is a pulmonary edema monitoring apparatus, which is always attached to the body and is capable of continuously monitoring whether a pulmonary edema occurs, for a patient with advanced disease or a shock patient. This pulmonary edema monitoring apparatus includes: an ultrasound frequency module which is attached to the chest of a patient, generates an ultrasound, and receives a reflection wave reflected from the inside of a human body; and a control module which measures the intensity (this is referred to as "ultrasound radio frequency data") of the reflection wave, determines whether a pulmonary edema occurs on the basis of an increasing rate of the ultrasound radio frequency data according to a degree of multiple reflection, and provides an alarm.

3 Claims, 5 Drawing Sheets

(52) U.S. Cl.
CPC .......... *A61B 8/4455* (2013.01); *A61B 8/4477* (2013.01); *A61B 8/46* (2013.01); *A61B 8/5223* (2013.01); *A61B 8/54* (2013.01)

(56) References Cited

U.S. PATENT DOCUMENTS

| | | | | |
|---|---|---|---|---|
| 2011/0130800 A1* | 6/2011 | Weinstein | ............ | A61B 5/6823 |
| | | | | 607/17 |
| 2014/0276083 A1* | 9/2014 | McKinnis | ................ | A61B 8/12 |
| | | | | 600/462 |
| 2015/0150503 A1 | 6/2015 | Pamnani et al. | | |
| 2017/0281097 A1* | 10/2017 | Thakur | ................ | A61B 5/7282 |

FOREIGN PATENT DOCUMENTS

| | | |
|---|---|---|
| KR | 10-2012-0117394 A | 10/2012 |
| KR | 10-2013-0089525 A | 8/2013 |

OTHER PUBLICATIONS

Korean Notice of Allowance dated Sep. 17, 2018, in connection with the Korean Patent Application No. 10-2017-0179547.
Korean Office Action dated Feb. 12, 2018, in connection with the Korean Patent Application No. 10-2017-0179547.

\* cited by examiner

PULMONARY EDEMA MONITORING APPARATUS

CROSS-REFERENCE TO RELATED APPLICATION

The present application is a national stage filing under 35 U.S.C § 371 of PCT application number PCT/KR2018/016404 filed on Dec. 21, 2018 which is based upon and claims the benefit of priority to Korean Patent Application No. 10-2017-0179547, filed on Dec. 26, 2017, in the Korean Intellectual Property Office, which is incorporated herein in its entirety by reference.

TECHNICAL FIELD

The present invention relates to a pulmonary edema monitoring apparatus, and more particularly, to a pulmonary edema monitoring apparatus which is always attached to the body and is capable of continuously monitoring whether a pulmonary edema occurs during treatment for a patient with advanced diseases or a shock patient.

BACKGROUND ART

The pulmonary edema is a disease which causes difficulty in breathing due to excessive accumulation of body fluids in mesopulmonum and alveoli. Pulmonary edemas are classified into a psychogenic type caused by a cardiac disease or disorder and a non-psychogenic type caused by other causes. The psychogenic pulmonary disease is caused by an increase in the hydrostatic pressure in pulmonary veins due to cardiac insufficiency, and causes of psychogenic cardiac insufficiency may also be diversified according to underlying cardiac diseases. In case of non-psychogenic pulmonary edema, an acute respiratory insufficiency syndrome is a representative case, and is caused by an increase in permeability of pulmonary capillaries.

In actual hospital, the pulmonary edema also occurs while treating a patient. For example, the basis of treatment of a patient with advanced disease or a shock patient is injection of a great amount of alimentation fluids. A pulmonary edema may occur during injection of a great amount of alimentation fluids to a patient with advanced disease, and the mortality increases by at least 10% due to the pulmonary edema itself. Thus, while performing alimentation to a patient, whether a pulmonary edema occurs should be monitored, but this is not practically easy. Specifically, in order to check a pulmonary edema, most widely performed inspection is chest X-ray examination, but it is almost impossible to continuously performing chest X-ray with respect to a patient with advanced disease or a shock patient.

DISCLOSURE OF THE INVENTION

Technical Problem

The present invention addresses the problem of providing a pulmonary edema monitoring apparatus, which is capable of continuously monitoring whether a pulmonary edema occurs, for a patient who is incapable of frequently taking chest X-ray.

Various problems to be addressed by the present invention are not limited to the aforesaid, but other problems not described herein will be clearly understood by those skilled in the art from descriptions below.

Technical Solution

In accordance with an embodiment of the present invention, a pulmonary edema monitoring apparatus includes: an ultrasound frequency module which is attached to the chest of a patient, generates an ultrasound, and receives a reflective wave reflected from the inside of a human body; and a control module which measures the intensity (hereinafter, referred to as "ultrasound radio frequency data") of the reflected wave, determines whether a pulmonary edema occurs on the basis of an increasing rate of the ultrasound radio frequency data according to a degree of multiple reflection, and provides an alarm.

The ultrasound frequency module may include: a probe in charge of generation and receipt of the ultrasound; and an attachment part arranged on a periphery of the probe and adhering to a skin, wherein a syringe may be pushed into an opening formed in the attachment part, and a gel may be injected into a space between the probe and the skin to minimize an acoustic resistance between the probe and the skin.

The control module may determine a pulmonary edema and provide an alarm when a relative ratio of the currently measured ultrasound radio frequency data increases to be greater than a predetermined value with respect to an initial ultrasound radio frequency data of a patient.

The ultrasound frequency module may include four ultrasound frequency modules, be always attached to intersections of fourth and fifth left and right intercostal space outer midclavicular lines and middle axillary lines, continuously measure and analyze the ultrasound radio frequency data at a period of several seconds to several minutes, and thus monitor whether a pulmonary edema occurs.

In accordance with another embodiment of the present invention, a pulmonary edema monitoring apparatus includes: an ultrasound frequency module which is attached to the chest of a patient, generates an ultrasound, and receives a reflection wave reflected from the inside of a human body; and a control module which measures the intensity (hereinafter, referred to as "ultrasound radio frequency data") of the reflection wave, determines whether a pulmonary edema occurs on the basis of an increasing rate of the ultrasound radio frequency data according to a degree of multiple reflection, and provides an alarm, wherein the control module does not process the reflection wave into a B-line image, but generates the ultrasound radio frequency data on the basis of raw data of the reflection wave, and the control module may determine a pulmonary edema and provide an alarm when a relative ratio (=(measured USRF data)/(initial USRF data)) of the currently measured ultrasound data (this is referred to as "measured USRF data") with respect to an initial USRF data of a patient increases to be greater than a predetermined value.

Specific matters of other embodiments are included in the detailed description and drawings.

Advantageous Effects

As described above, a pulmonary edema monitoring apparatus according to the present invention may continuously monitor whether a pulmonary edema occurs due to injection of a great amount of alimentation fluids. That is, such patients are in a situation of being incapable of frequently taking chest X-ray, and thus, whether a pulmonary edema occurs should accurately be determined while lying in a hospital bed. An ultrasound radio frequency module according to the present invention is designed so as to be easily attached to a chest portion in a small disk shape, and therefore a patient does not necessarily move separately, and whether a pulmonary edema occurs may continuously be monitored.

In addition, a pulmonary edema monitoring apparatus according to the present invention determines whether a pulmonary edema occurs on the basis of the amount of increase or the rate thereof with respect to the intensity of the reflected ultrasound reflected inside a lung portion, that is, the ultrasound radio frequency (USRF) data, and thus, the configuration of the apparatus is simple and the treatment processing is quick. That is, it is not necessary to separately process images and display an ultrasound result, but it is only need to generate a pulmonary edema occurrence alarm on the basis of increase or decrease in the ultrasound radio frequency data. If an alarm is generated while a patient is taking injection of a great amount of alimentation fluid in a state in which a pulmonary edema monitoring apparatus is attached to the patient, a doctor determines the occurrence of a pulmonary edema, stops injection of alimentation fluids, and immediately treat a pulmonary edema using a cardiant, a pressor agent, a diuretic, or the like. That is, the occurrence of pulmonary edema caused by injection of a great amount of alimentation fluids and the morality due to the pulmonary edema may remarkably be reduced.

MODE FOR CARRYING OUT THE INVENTION

Figure 1:
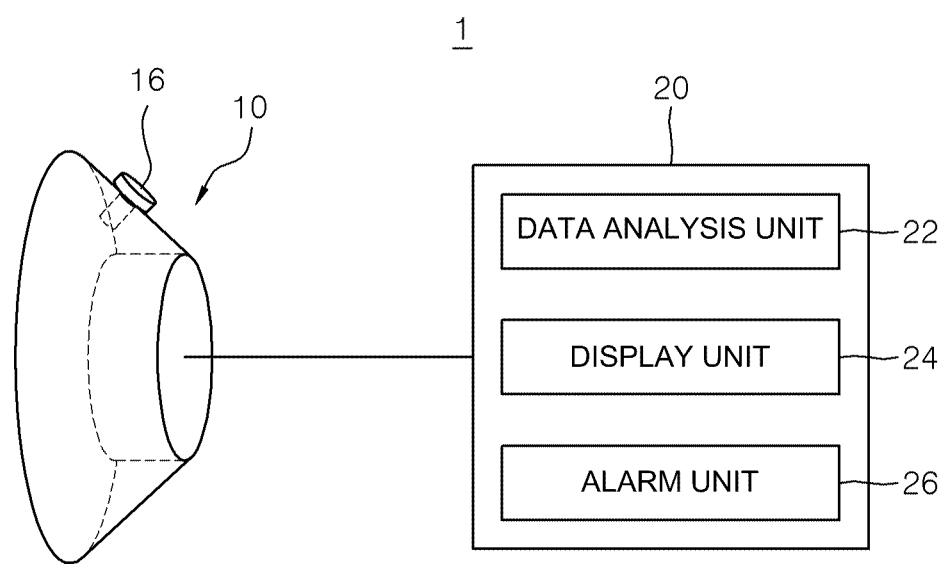
FIG. 1 is a configuration view of a pulmonary edema monitoring apparatus according to an embodiment of the present invention.

Advantages and features of the present invention, and implementation methods thereof will be clarified through following embodiments described with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims. Like reference numerals refer to like elements throughout.

Hereinafter, with reference to FIGS. 1 and 3, the configuration of a pulmonary edema monitoring apparatus according to an embodiment of the present invention will be described in detail. FIG. 1 is a configuration view of a pulmonary edema monitoring apparatus according to an embodiment of the present invention, FIG. 2 is a cross-sectional view of an ultrasound frequency module of FIG. 1, and FIG. 3 illustrates an example in which the ultrasound frequency module of FIG. 1 is attached to a human body.

Referring to FIG. 1, a pulmonary edema monitoring apparatus 1 of the present invention includes: an ultrasound frequency module 10 which is attached to the chest of a patient, generates an ultrasound, and receives a reflective wave reflected from the inside of a human body; and a control module 20 which measures the intensity (ultrasound radio frequency (USRF) data) of the reflected wave, determines whether a pulmonary edema occurs on the basis of an increasing rate of the ultrasound radio frequency data according to a degree of multiple reflection, and provides an alarm.

Figure 2:
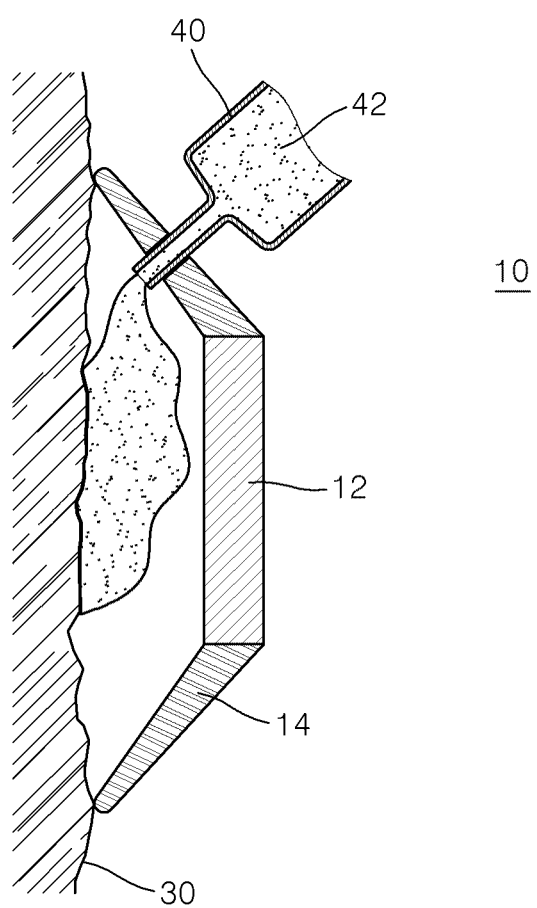
FIG. 2 is a cross-sectional view of an ultrasound frequency module.
Figure 3:
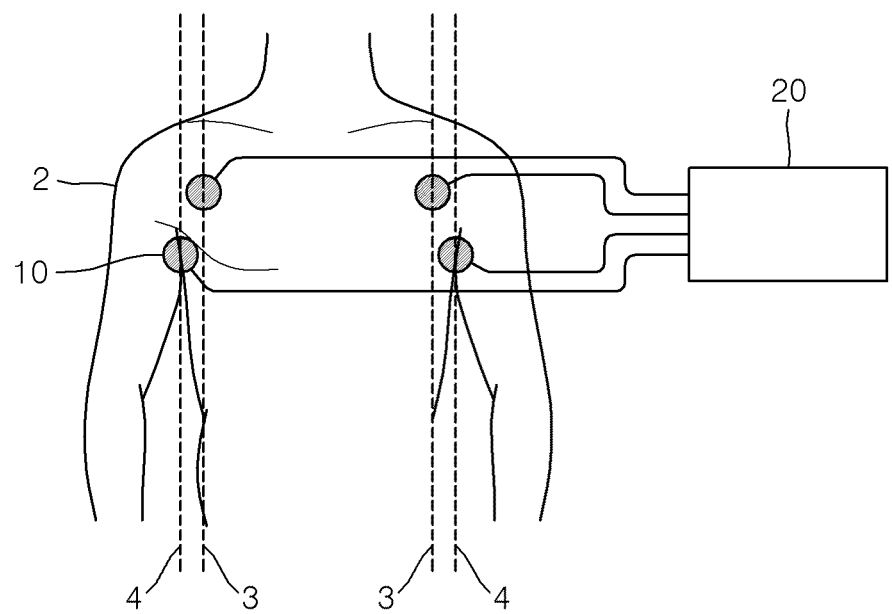
FIG. 3 illustrates an example in which the ultrasound frequency module is attached to a human body.

Referring to FIG. 2, an ultrasound frequency module 10 includes a probe 12 which is in charge of generation and receipt of ultrasound and an attachment part 14 which is arranged on the periphery of the probe and adheres to a skin 30.

The probe 12 is an apparatus which generates and transmits an ultrasound and receives reflected echo, that is, reflected wave. The probe 12 of the present invention should be always attached to the chest portion of a patient in order to monitor in real time whether a pulmonary edema occurs, and therefore be favorably formed in a disk shape having a diameter of, for example, approximately 1 cm. The probe 12 functions to convert electrical energy into a sound wave, receive reflected sound, and convert the reflected sound into electrical energy. To this end, the probe 12 may be formed of a piezoelectric material. The energy generated in the probe 12 may have a frequency of 2 MHz to 4 MHz. The probe 12 generates an ultrasound for every several seconds to several minutes, for example, for every 5 seconds to 1 minute, measures a reflected wave of the ultrasound, and records ultrasound radio frequency data. The ultrasound radio frequency data is unprocessed sound wave signal data, and may be understood as raw data of brightness mode (B mode) in an ultrasound image generally used in an ultrasound diagnosis apparatus. In addition, the ultrasound radio frequency data may also be understood as the amplitude of a reflected wave, and may also be understood as the intensity of the reflected wave, that is, as power (W/cm$^2$) of sound wave per unit area.

The attachment part 14 is formed on the periphery of the probe 12 and comes into contact with a skin 30. The attachment part 14 may be formed of a material having adhesiveness or be coated with a material having adhesiveness. An opening formed in the attachment part 14 is sealed by a cap 16. When a space is generated between the probe 12 and the skin 30, acoustic resistance increases due to a difference in the densities of materials, and therefore it is difficult to accurately measure an ultrasound radio frequency data. Here, the acoustic resistance is a fundamental characteristic of a material and is defined as the product of the density of the material and the speed of a sound wave. It is known that reflectivity between a soft tissue and air is the largest. Thus, when measuring data, it is desirable to open the cap 16, push in a syringe 40 through the opening, inject a gel 42 into a space between the probe 12 and the skin 30 through the syringe 40, and thus minimize acoustic resistance between the probe 12 and the skin 30. When the gel 42 is sufficiently injected into the space, the opening is closed by the cap 16 to prevent the gel 42 from leaking to the outside.

Referring to FIG. 3, an ultrasound frequency module is configured from, for example, four modules, is always attached to intersections of fourth and fifth left and right intercostal space outer midclavicular lines 3 and middle axillary lines 4, and continuously measures the ultrasound radio frequency data.

Referring again to FIG. 1, the control module 20 includes: a data analysis unit 22 which analyzes the ultrasound radio frequency data received from the ultrasound frequency module 10 and determines whether a pulmonary edema occurs; a display unit 24 which displays the ultrasound radio frequency data; and an alarm unit 26 which provides a warning alarm through a voice, an image, or the like when determining a pulmonary edema.

Figure 4:
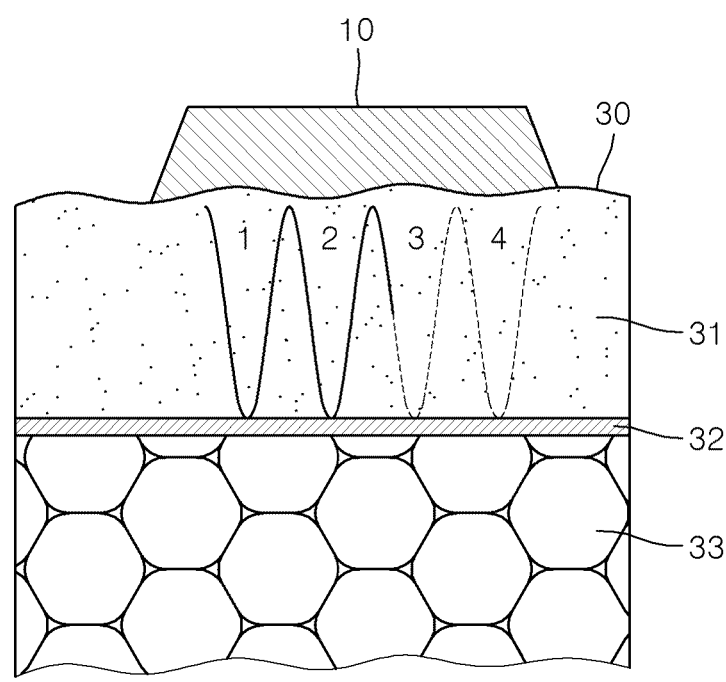
FIG. 4 is a view illustrating multiple reflection between a pleura and alveoli.
Figure 5:
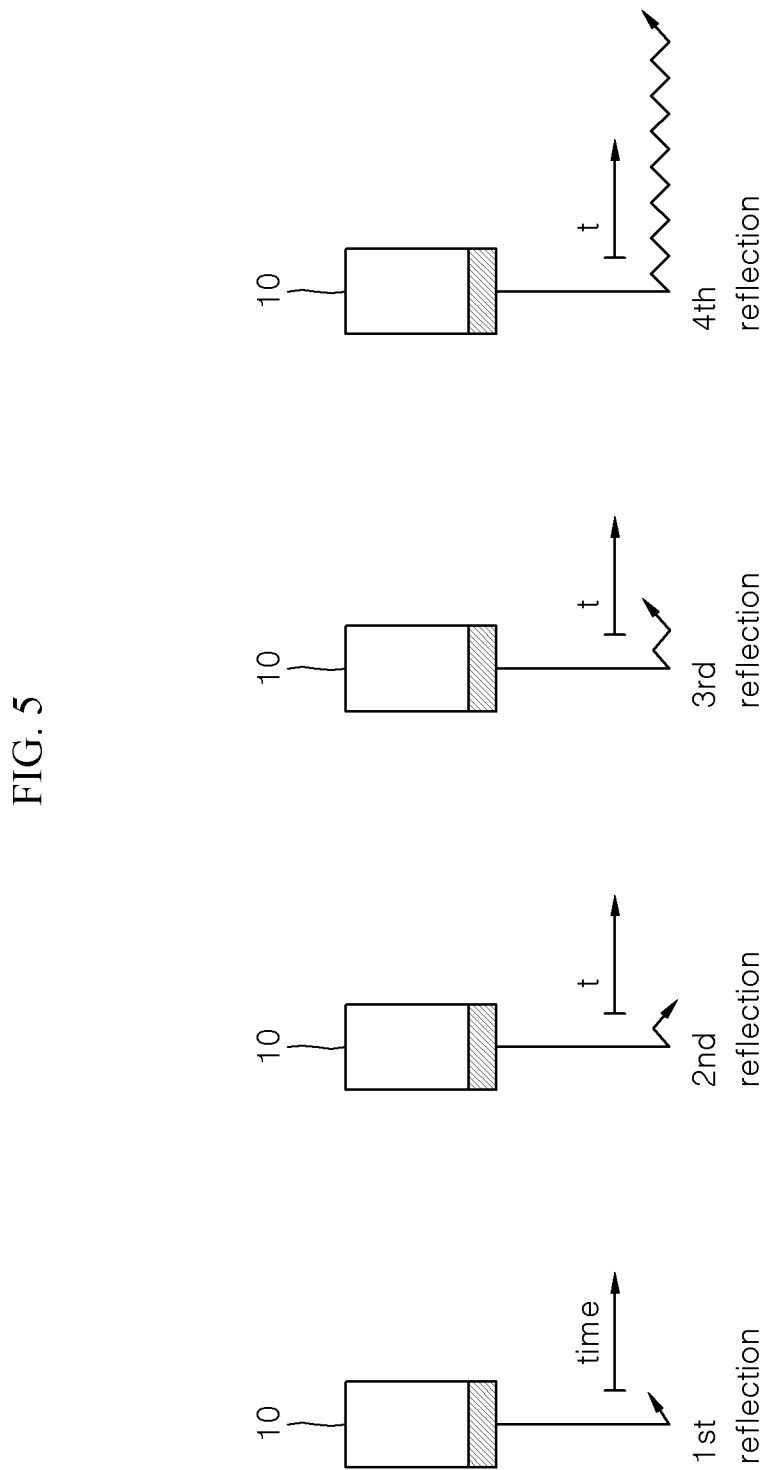
FIG. 5 is a view illustrating an increase in the intensity of a reflected wave due to multiple reflection.

Referring to FIGS. 4 and 5, a method will be described in detail with which a pulmonary edema monitoring apparatus according to the present invention determines whether a pulmonary edema occurs. FIG. 4 is a view illustrating multiple reflection between a pleura and alveoli, and FIG. 5 is a view illustrating an increase in the intensity of a reflected wave due to multiple reflection.

A sound wave returned from an interface having a large difference in acoustic resistance is received with an increased amplitude, and a phenomenon in which such an ultrasound is repeated between a reflective object and the probe 12 until energy is attenuated is referred to as multiple reflection. Referring to FIG. 4, multiple reflection occurs when there are two or more interfaces which are perpendicular to an ultrasound beam and parallel to the surface of the skin 30. A place where the multiple reflection most frequently occurs is between a pleura 32 and alveoli 33. In the human body, a soft tissue 31, that is, a subcutaneous layer, a fascia, muscle, and the like are present between the skin 30 and the pleura 32, and the ultrasound wave easily passes through the soft tissue 31. However, since the lung is a human organ at least 90% of which is filled with air, the ultrasound reaching the pleura 32 is mostly reflected because the difference in the acoustic resistance of the soft tissue 31 and the alveoli 33 is large. Reflected ultrasound (that is, reflected wave) collides with the ultrasound frequency module 10. Here, ultrasound is reflected again due to the difference in acoustic resistance between the surface of the probe 12 and the soft tissue 31, and reflected again at the pleura 32. As such, multiple reflection occurs between the ultrasound frequency module 10 and the pleura 32.

Meanwhile, when a pulmonary edema occurs, water is filled into the alveoli 33, and alveoli filled with water and alveoli not filled with water are present together. Since there is a large difference in acoustic resistance between the alveoli filled with water and the alveoli not filled with water, multiple reflection also occurs between the alveoli. That is, the further the pulmonary edema advances, the greater the number of alveoli filled with water, and thus, multiple reflection increases. As illustrated in FIG. 5, the greater the number of reflections, the greater the amplitude of the sound wave, and thus, the value of ultrasound radio frequency (USRF) data also increased.

The data analysis unit 22 of the present invention determines whether a pulmonary edema occurs by using the fact that the USRF data increases when a pulmonary edema occurs. That is, the data analysis unit 22 compares the continuously measured USRF data of a patient with respect to the initial USRF data of the patient, and when the relative ratio of the currently measured USRF data with respect to the initial USRF data increases up to a predetermined value, for example, increases up to at least 3 to 4 times, occurrence of a pulmonary edema is determined.

Figure 6:
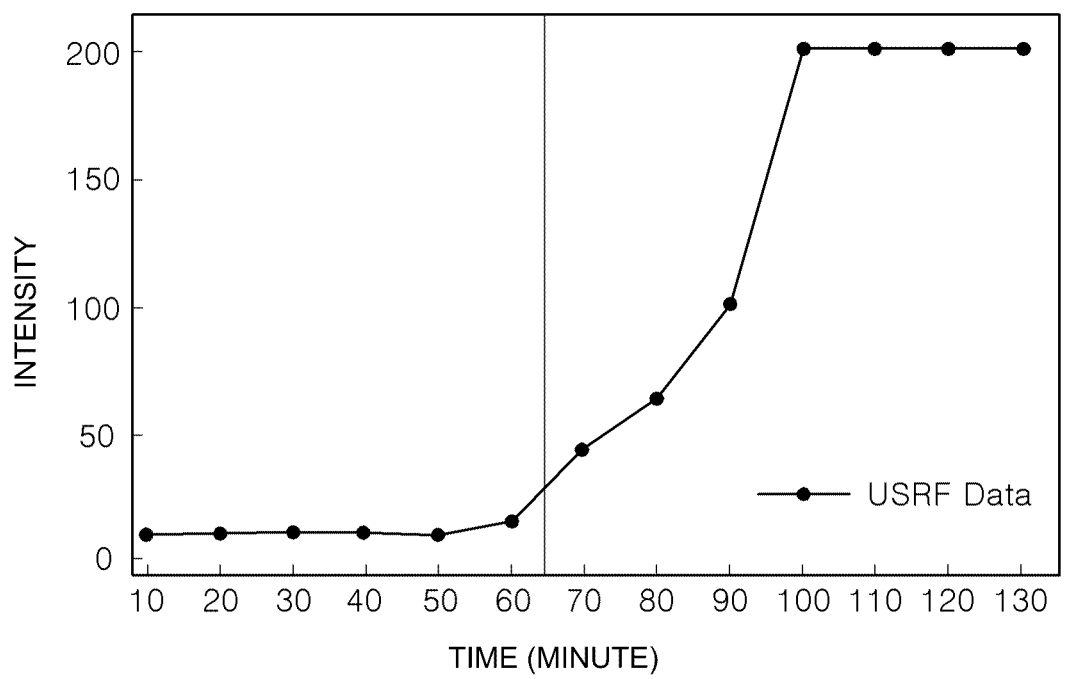
FIG. 6 is a graph illustrating an animal experiment result using a pulmonary edema monitoring apparatus according to an embodiment of the present invention.

FIG. 6 is a graph illustrating an animal experiment result using a pulmonary edema monitoring apparatus according to an embodiment of the present invention. Specifically, a 40 Kg pig was selected as an experiment object, and while injecting 6 mL of normal saline solution per minute for pig weight of 1 kg (that is, 6 mL/kg/min), the USRF data was measured for every 10 minutes. That is, a relative value of the amplitude or the intensity of reflected wave was measured. For initial 50 minutes, there were no change in the USRF data, and a pulmonary edema phenomenon did not occur. When 60 minutes elapsed, an increase in the USRF data was measured, a suspected symptom of pulmonary edema appeared. Subsequently, from the time when 70 minutes elapsed, the USRF data rapidly increased, and a pulmonary edema occurred. Here, it was understood that from the time when the measured USRF data with respect to the initial USRF data increased up to approximately 3-4 times, the pulmonary edema advanced.

Figure 7:
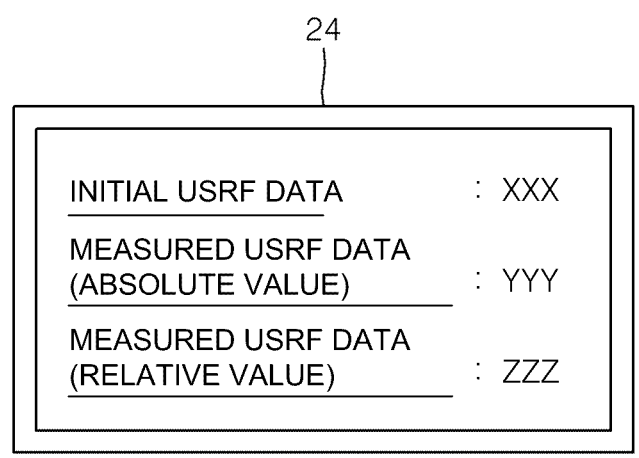
FIG. 7 exemplarily illustrates a screen of a display unit of FIG. 1.

FIG. 7 exemplarily illustrates a screen of the display part of FIG. 1. As illustrated in FIG. 7, a pulmonary edema monitoring apparatus of the present invention may display the USRF data (initial USRF data) measured in the initial lung state of a patient and the currently measured USRF data (absolute value), and may calculate the relative ratio therebetween (=(measured USRF data (absolute value)/(initial USRF data)) and display the relative ratio as the measured USRF data (relative value). Since expressed as a simple numerical value as such, a doctor may intuitively determine whether a pulmonary edema occurs by only checking the relative ratio.

The above-disclosed subject matter is to be considered illustrative and not restrictive, and the appended claims are intended to cover all such modifications, enhancements, and other embodiments, which fall within the true spirit and scope of the inventive concept. Thus, to the maximum extent allowed by law, the scope of the inventive concept is to be determined by the broadest permissible interpretation of the following claims and their equivalents, and shall not be restricted or limited by the foregoing detailed description. Thus, the above-disclosed embodiments are to be considered illustrative and not restrictive.

The invention claimed is:

1. A pulmonary edema monitoring apparatus comprising:
   an ultrasound frequency module configured to be attached to a chest of a patient, generate an ultrasound at every predetermined time, and receive a reflected wave of the ultrasound reflected from an inside of the chest of the patient for a predetermined duration; and
   wherein the pulmonary edema monitoring apparatus programmed to measure an intensity of the reflected wave at every predetermined time,
   compare the measured intensity of the reflected wave with an initial reflected wave,
   determine that a pulmonary edema has occurred when a relative ratio of the measured intensity of the reflected wave to the initial reflected wave increases to be greater than a predetermined value for the predetermined duration, and
   output an alarm based on the determination of the pulmonary edema.

2. The pulmonary edema monitoring apparatus of claim 1, wherein the ultrasound frequency module comprises:
   a probe configured to generate the ultrasound and receive the reflected wave; and
   an attachment part arranged on a periphery of the probe and configured to be attached to a skin of the patient, wherein a syringe is pushed into an opening formed in the attachment part, and a gel is injected into a space between the probe and the skin to minimize an acoustic resistance between the probe and the skin.

3. The pulmonary edema monitoring apparatus of claim 1, wherein the ultrasound frequency module comprises four ultrasound frequency modules configured to be attached to intersections of fourth and fifth of left and right intercostal space outer midclavicular lines and middle axillary lines, respectively.

* * * * *